United States Patent [19]

Alonso et al.

[11] 4,382,919
[45] May 10, 1983

[54] COMPOSITION FOR TREATMENT AND PREVENTION OF MALODOROUS GENERATING SKIN CONDITIONS

[75] Inventors: Richard J. Alonso; Ara Nersesian, both of Livingston; Val F. Cotty; S. Mark Henry, both of Westfield, all of N.J.

[73] Assignee: Bristol-Myers Company, New York, N.Y.

[21] Appl. No.: 187,255

[22] Filed: Sep. 15, 1980

[51] Int. Cl.³ ............ A61K 7/00; A61K 7/32; A61K 31/74; A61K 31/745

[52] U.S. Cl. .................. 424/65; 424/47; 424/69; 424/78; 424/83

[58] Field of Search ............ 424/47, 65, 69, 78, 424/83

[56] References Cited

U.S. PATENT DOCUMENTS

| | | | |
|---|---|---|---|
| 2,512,616 | 6/1950 | Eberl et al. | 424/78 |
| 2,688,586 | 9/1954 | Eberl et al. | 424/127 |
| 3,133,866 | 5/1964 | Richardson | 424/65 |
| 3,201,315 | 8/1965 | Daglish et al. | 424/250 |
| 3,266,992 | 8/1966 | de Joug | 424/14 |
| 3,320,133 | 5/1967 | Sugo et al. | 424/78 |
| 3,321,408 | 5/1967 | Briggs | 252/161 |
| 3,424,842 | 1/1969 | Nurnberg | 424/94 |
| 3,835,169 | 9/1974 | Kraft et al. | 424/365 |
| 3,836,665 | 9/1974 | Eberhardt et al. | 424/47 |
| 3,843,701 | 10/1974 | Wortham | 424/76 |
| 3,846,382 | 11/1974 | Ramsey et al. | 260/78.3 R |
| 3,860,700 | 1/1975 | Viout et al. | 424/61 |
| 3,879,560 | 4/1975 | Kalopissis | 424/47 |
| 3,903,259 | 9/1975 | Hart | 424/76 |
| 3,911,105 | 10/1975 | Papantoniou et al. | 424/64 |
| 3,920,015 | 11/1975 | Wortham | 424/76 |
| 3,953,590 | 4/1976 | Douglass et al. | 424/65 |
| 3,953,591 | 4/1976 | Snyder | 424/73 |
| 3,961,044 | 6/1976 | Kelly et al. | 424/78 |
| 3,964,486 | 6/1976 | Blaney | 424/28 |
| 3,966,902 | 6/1976 | Chromecek | 424/59 |
| 4,003,990 | 1/1977 | Jacquet et al. | 424/78 |
| 4,034,077 | 7/1977 | Hill et al. | 424/69 |
| 4,036,991 | 7/1977 | Stiefel | 424/47 |
| 4,053,630 | 10/1977 | Yu et al. | 424/65 |
| 4,275,054 | 6/1981 | Sebag et al. | 424/65 |

FOREIGN PATENT DOCUMENTS

| | | |
|---|---|---|
| 709091 | 8/1952 | United Kingdom . |
| 2007090 | 5/1979 | United Kingdom . |
| 2017491 | 10/1979 | United Kingdom . |
| 2023000 | 12/1979 | United Kingdom . |
| 2029224 | 3/1980 | United Kingdom . |

OTHER PUBLICATIONS

The March Index, 9ed, (1976) p. 915.
The Extra Pharmacopoeia, Martindale, 27th Edition, pp. 89-90; 919 and 1717.
The British Pharmaceutical Codex, 11th Edition, p. 141.

*Primary Examiner*—Allen J. Robinson
*Attorney, Agent, or Firm*—Irving Holtzman; George A. Mentis; Gabriel P. Katona

[57] ABSTRACT

A composition and treatment to prevent the symptoms of skin conditions characterized by an offensive odor of the body, such as diaper rash, perspiration odor and athlete's foot. The composition contains as the active ingredient a non-toxic, high molecular weight organic polymeric acid which is not absorbed through the skin. Treatment is by topical application of a dusting powder, aerosol spray, cream or ointment containing 1 to 30% by weight of a high molecular weight organic polymeric acid such as alignic acids, Carbopol resins or other polymeric acids.

10 Claims, No Drawings

COMPOSITION FOR TREATMENT AND PREVENTION OF MALODOROUS GENERATING SKIN CONDITIONS

BACKGROUND OF THE INVENTION

The present invention relates to the treatment of skin conditions characterized by malodor of the body, and specifically to the use of compositions containing an effective amount of a non-toxic, high molecular weight organic polymeric acid active ingredient which when topically applied to the skin is substantially not absorbed and which achieves a complete or substantially complete prevention of the formation of malodor from the treated body areas. The non-toxic, high molecular weight organic polymeric acid ingredient of the present invention can conveniently be applied in the form of dusting powders, ointments, creams and aerosol sprays. The invention more particularly relates to the application to a baby's skin of a dry, free-flowing dusting powder composition containing an effective amount of the active ingredient to eliminate the unpleasant odor of ammonia associated with the decompositions of urea in a baby's urine and to prevent diaper rash. The invention further relates to the topical application of a free-flowing dusting powder to skin areas of axilla and feet to prevent malodor and to treat athlete's foot.

DESCRIPTION OF THE PRIOR ART

Malodor in infants can be caused when the infant's diaper is wet with urine which is decomposed due to the action of bacteria to form ammonia, and malodor of adults to a large extent is the consequence of perspiration of the skin in the axilla and feet regions of the body. The glands in these areas secrete organic substances which are degraded by microbial attack to produce organic compounds, including ammonia, having unpleasant odors. In addition, athlete's foot disease frequently evidenced by cracking, flaking and itching of the feet is also accompanied by unpleasant odor.

Diaper rash is the most common form of irritation and inflammation of an infant's skin. When a diaper is wet with urine, the urea contained in the fluid, though not normally irritating, decomposes due to the action of bacteria to produce ammonia. The ammonia is very irritating to the infant's tender skin and is the primary contributor to the unpleasant odor which develops. The ammonia has a pH considerably above 7 which causes the irritation of the baby's skin. An approach that has been used to prevent diaper rash was to employ germicides to destroy the bacteria responsible for decomposition of the urea, but frequently it was found that the germicides used were almost as irritating to the baby's skin as the ammonia they were to eliminate.

Another approach that has been used to prevent diaper rash was to incorporate in the diaper structure low molecular weight organic carboxylic acids to inhibit microbial growth and ammonia formation. The low molecular weight organic carboxylic acids that have been used for this purpose include citric, maleic, malonic, succinic, tartaric and fumaric. It has, however, not been discovered that several of these acids dissolve too rapidly, over-neutralize the ammonia and result in an excessively low pH, i.e. high acid concentration, which itself causes substantial irritation of the baby's skin, and in addition, several of the acids are potentially dangerous to the baby in that they may be absorbed through the baby's skin.

The malodor in adults which is the consequence of perspiration of the skin in the axilla region of the body has been treated by the application of deodorant and/or antiperspirant products. Many deodorant and antiperspirant products on the market today contain as the active ingredient salts of aluminum, zinc or zirconium. The aluminum salts include aluminum chloride, aluminum chlorhydroxide, aluminum sulfate, aluminum potassium sulfate, and aluminum phenol sulfonate. The zinc salts comprise zinc oxide, zinc peroxide, zinc stearate, and zinc phenol sulfonate. Although long term use of aluminum or zinc salts as underarm deodorants present no major problem in toxicity, these compounds do frequently cause irritation, burning, itching and other uncomfortable side effects. Consequently, many people have stopped using existing underarm deodorants available on the market today because of the persistent itching or burning effect after use.

The development of effective deodorant substances which do not cause irritation, itching or uncomfortable side effects when applied to the skin is therefore desirable.

SUMMARY OF THE INVENTION

It has now been discovered that conditions characterized by offensive odor, such as diaper rash, perspiration and athlete's foot may be successfully prevented by the application of a composition containing as the active ingredient an effective amount of a non-toxic high molecular weight organic polymeric acid to the treated area. The high molecular weight organic polymeric acid, when applied to the human skin in the amount specified, has no harmful effects on the skin of an infant or an adult. A treatment by the topical application of a composition containing the active ingredient to skin areas of crotch, axilla and feet has been found to prevent diaper rash, axillary and foot odor, and to alleviate athlete's foot.

The non-toxic, high molecular weight organic polymeric acids can be topically applied in the form of powders, ointments, aerosol sprays or creams. The preferred non-toxic, high molecular weight organic polymeric acids are alginic acid and Carbopol resins. The preferred method of application is in the form of a dusting powder containing 1% to 30% by weight of the active ingredient. The dusting powders, when used, can be advantageously applied to a baby's skin to prevent diaper rash and to prevent the formation of ammonia and the bad odor accompanying a diaper wet with urine; to the axilla and feet areas of the body to prevent perspiration odor; and to the feet area of the body to treat athlete's foot.

DETAILED DESCRIPTION OF THE INVENTION

The compositions of the present invention contain as the active ingredient a non-toxic, high molecular weight organic polymeric acid which is not, or is substantially not absorbed through the skin. The polymeric acids which can be used in accordance with the present invention are alginic acid, Carbopol resins, carboxymethylcellulose (free acid), poly(methyl vinyl ether/maleic acid), poly(styrene maleic acid), and pectin.

The alginic acid and Carbopol resins are preferred, and the alginic acid is particularly preferred because of its low toxicity and because it is only very slightly soluble in water.

The non-toxic, high molecular weight organic polymeric acids of the present invention can be made into stable, finely divided, non-caking and free-flowing powders. They have a high ammonia neutralizing capacity, high moisture absorbing capacity and in some instances, because of their low acidity, can control microbial proliferation.

Alginic acid, polymer of D-mannuronic acid and L-guluronic acid, is extracted from certain seaweed plants by processes which are well known in the art. Pure alginic acid has a pH of 2.8 and is very slightly soluble in water. Alginic acid, depending on the seaweed plants from which it is extracted, can have a molecular weight of 15,000 to 900,000. Alginic acid has very low toxicity, is readily available commercially (as Kelacid from Kelco M.W. 15,000 to 240,000) and easily forms stable, finely divided, non-caking, free-flowing powders which have a high moisture absorbant capacity.

Carbopol resins are carboxy vinyl polymers sold by the B. F. Goodrich Company under the trademark CARBOPOL 934, 940 and 941. These polymeric resins consist essentially of synthetic, hydrophilic colloids which are water-soluble and which are available in the form of white, free-flowing acid powders. A 1% solution of the polymeric resin in water has a pH of 3. The polymeric resin powders have low acute oral toxicity and are not irritant or allergenic. The Carbopol resins are polymers of acrylic acid cross-linked with from 0.75% to 2% of a cross-linking agent selected from the class consisting of polyallyl sucrose and polyallyl pentaerythritol and have a molecular weight of from 450,000 to 5,000,000.

A preferred polymer is Carbopol 934 which has an average molecular weight of about 3,000,000. Carbopol 934 is a water-soluble polymer of acrylic acid cross-linked with about 1% of polyallyl ether of sucrose of an average of about 5.8 allyl groups for each sucrose molecule. Another preferred Carbopol resin is Carbopol 941 which has an average molecular weight of about 1,250,000. Carbopol 941 is a water-soluble polymer of acrylic acid cross-linked with polyallyl ether of sucrose similar to Carbopol 934.

Additional high molecular weight polymeric acids that could be used in the invention are the following:

Poly(vinyl ether-maleic anhydride)

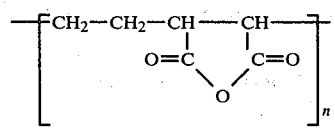

Monsanto CX-840-91 (EMA 91) (CTFA nomenclature Ethylene/Maleic Anhydride Copolymer)

Poly(vinyl ether-maleic acid)

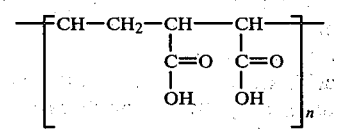

Monsanto (EMA 21)

Poly(methylvinyl ether-maleic anhydride)

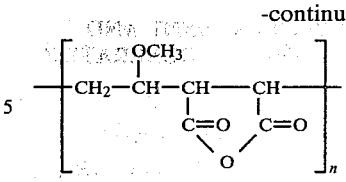

G.A.F. Gantrez AN Series

Poly(methylvinyl ether-maleic acid)

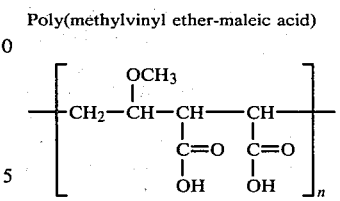

G.A.F. Gantrez HY Series

The high molecular weight polymeric acids of the present invention because of their high molecular weight are less prone to percutaneous absorption, less toxic and less irritating. They tend to be bacteriostatic by virtue of their high acidity.

The polymeric acids of the present invention differ from other deodorant compounds in that they are not potent bactericides nor are they odor neutralizers. They act by intensifying the normal acidity of the skin and, secondly, as strong absorbants of moisture. They impart high ammonia neutralizing capabilities to areas to be treated, such as diaper area in infants and axilla in adults without compromising toxicological safety.

The active ingredient is used in an effective odor neutralizing amount of 1 to 30% by weight, preferably 2 to 20% by weight and more preferably, 4 to 10% by weight of the composition.

The compositions of the present invention contain a major proportion of a pharmaceutical carrier and can optionally contain emulsifiers dispersing and wetting agents, oils, emollients and fragrances, and an agent to render the powders anti-caking and free-flowing.

The compositions of the present invention may also contain compounds which function as anti-bacterial agents to combat bacteria which cause diaper rash, perspiration odor and/or athlete's foot. The anti-bacterial compounds may be present in an anti-bacterially effective amount of from 0.025 to 2% by weight, preferably 0.05 to 1% by weight. Examples of suitable anti-bacterial compounds are 8-hydroxyquinoline, methylbenzethonium chloride, benzethonium chloride, benzalkonium chloride, and the like.

The dusting powder as well as the ointment composition may contain zinc oxide which in addition to acting as a whitening agent also imparts astringent properties. The zinc oxide may be present in an amount of 1 to 30% by weight, preferably 5 to 20% by weight of the composition.

Where a dusting powder composition is desired, the composition can contain a major proportion of a pharmaceutical carrier, such as talc and/or a dry-flow starch which serves to repel moisture and helps to keep the skin smooth and dry. The talc and/or dry-flow starch can be employed in amounts of from about 70 to 99% by weight, preferably from 80 to 98% by weight and more preferably 90 to 96% by weight of the composition. In addition, small amounts, for example, from about 0.5 to 4% by weight, preferably 0.1 to 2% by weight of a hydrophobic silicon dioxide can be added to impart free-flowing properties and to aid in repelling moisture. Other ingredients such as perfume fragrances may be incorporated in quantities sufficient to impart the desired effect.

Where an ointment composition is desired, the ointments may contain a gelled mineral oil or petrolatum base in an amount of from 70 to 99% by weight, preferably 80 to 98% by weight and more preferably 90 to 96% by weight of the composition. The mineral oil is gelled with a polyalkylene material, e.g. polyethylene. The ointment composition may also contain a liquid emollient, such as, for example, acetylated lanolin or cod liver oil. The ointment compositions of the present invention may be prepared in a conventional manner by blending the added ingredients into a gelled mineral oil until a uniform mixture is obtained. Other ingredients such as perfume fragrances may, as before, be incorporated in quantities sufficient to impart the desired effect of the ointment.

The following are illustrative Examples of formulations of compositions made according to this invention. Although the Examples utilize only selected members of the above listed materials, useful according to this invention, it should be understood that the following Examples are illustrative and not limiting.

EXAMPLE 1

| Ingredient | Powder % by Wt. |
|---|---|
| Alginic acid* | 4.55 |
| Talc | 47.68 |
| Starch | 47.77 |
|  | 100.00 |

*Kelacid (Kelco) M.W. 15,000 to 240,000

EXAMPLE 2

| Ingredient | Powder % by Wt. |
|---|---|
| Alginic acid* | 4.55 |
| Talc | 45.06 |
| Starch | 41.00 |
| 8-Hydroxyquinoline | 0.10 |
| 8-Hydroxyquinoline sulfate | 0.05 |
| Zinc oxide | 9.10 |
| Fragrance | 0.14 |
|  | 100.00 |

*Kelacid (Kelco) M.W. 15,000 to 240,000

EXAMPLE 3

| Ingredient | Powder % by Wt. |
|---|---|
| Alginic acid* | 2.00 |
| Talc | 47.61 |
| Starch | 41.00 |
| 8-Hydroxyquinoline | 0.10 |
| 8-Hydroxyquinoline sulfate | 0.05 |
| Zinc oxide | 9.10 |
| Fragrance | 0.14 |
|  | 100.00 |

*Kelacid (Kelco) M.W. 15,000 to 240,000

EXAMPLE 4

| Ingredient | Powder % by Wt. |
|---|---|
| Alginic acid* | 2.00 |
| Talc | 47.61 |
| Starch | 41.12 |
| Zinc Oxide | 9.10 |
| Fragrance | 0.17 |
|  | 100.00 |

*Kelacid (Kelco) M.W. 15,000 to 240,000

EXAMPLE 5

| Ingredient | Powder % by Wt. |
|---|---|
| Carbopol 941 polymeric acid | 4.55 |
| Talc | 47.68 |
| Starch | 47.77 |
|  | 100.00 |

EXAMPLE 6

| Ingredient | Powder % by Wt. |
|---|---|
| Carbopol 941 polymeric acid | 4.55 |
| Talc | 45.06 |
| Starch | 41.00 |
| 8-Hydroxyquinoline | 0.10 |
| 8-Hydroxyquinoline sulfate | 0.05 |
| Zinc oxide | 9.10 |
| Fragrance | 0.14 |
|  | 100.00 |

EXAMPLE 7

| Ingredient | Ointment % by Wt. |
|---|---|
| Alginic acid* | 10.0 |
| Cod liver oil | 5.0 |
| Acetylated lanolin | 2.0 |
| Mineral oil gelled with 5% polyethylene | 82.8 |
| Perfume | 0.2 |
|  | 100.0 |

*Kelacid (Kelco) M.W. 15,000 to 240,000

EXAMPLE 8

The dusting powder composition of Example 4 containing 2% by weight of alginic acid when diluted to 0.4% by weight concentration of alginic acid in urine maintained an acid pH for up to 48 hours. When the alginic acid concentration was increased to 5% by weight of the dusting powder composition, a pH of about 3.0 was imparted to the urine. In other tests using sterilized urine reinoculated with urea splitting bacteria, it was unexpectedly found that 0.5% by weight of alginic acid inhibited bacterial growth.

EXAMPLE 9

Tests were carried out on infants using the composition of Example 3 and it was found that the composition was significantly better overall than a non-medicated baby powder in relieving dryness and diaper rash.

EXAMPLE 10

The dusting powder composition of Example 3 was tested as an underarm deodorant by topical application to the axilla region and was found effective in inhibiting axillary odor for approximately 12 hours.

EXAMPLE 11

The dusting powder composition of Example 3, when topically applied to feet infected with athlete's foot disease, significantly improves the cracking, flaking and itching of athlete's foot during the period of twice daily treatment.

EXAMPLE 12

The dusting powder composition of Example 5, when topically applied to an infant, was found to have good ammonia neutralizing properties and to control microbial proliferation.

| | Aerosol Sprays | |
|---|---|---|
| Ingredient | EX. 13 % by wt. | EX. 14 % by wt. |
| Alginic acid* | 2.0 | — |
| Carbopol 941 | — | 1.0 |
| Cab-O-Sil M-5 | 1.0 | 1.0 |
| Talc | 8.5 | 8.5 |
| Powdertrol** | 1.0 | 1.0 |
| Fragrance | 0.1 | 0.1 |
| Aerothene TT*** | 87.4 | 88.4 |
| | 100.0 | 100.0 |

*Kelacid (Kelco) M.W. 15,000 to 240,000
**Powdertrol (Malmstrom Co.) 65% liquid fraction of lanolin and 35% of inert calcium silicate powder
***1,1,1-trichloroethane (Dow Chemical Co.)

| | Powders | |
|---|---|---|
| Ingredient | EX. 15 % by Wt. | EX. 16 % by Wt. |
| Alginic acid* | 5.0 | 2.5 |
| Starch | 15.0 | 15.0 |
| Zinc oxide | 10.0 | 10.0 |
| Benzethonium chloride | 0.2 | — |
| Carbopol 941 | — | 2.5 |
| Talc | 69.8 | 70.0 |
| | 100.0 | 100.0 |

*Kelacid (Kelco) M.W. 15,000 to 240,000

EXAMPLE 17

| | Cream |
|---|---|
| Ingredient | % by Wt. |
| Glyceryl monostearate | 9.0 |
| Cetyl alcohol | 4.0 |
| Isopropyl myristate | 2.0 |
| Steareth-20 | 2.0 |
| Propylene glycol | 5.0 |
| Alginic acid* | 2.0 |
| Deionized water | 76.0 |
| | 100.0 |

Applicants have found that compositions containing as an active ingredient a non-toxic, high molecular weight organic polymeric acid which is not substantially absorbed through the skin can be used in a treatment to prevent symptoms of skin conditions characterized by an offensive odor of the body, such as diaper rash, perspiration odor and athlete's foot. A treatment by the topical application of the composition containing Applicants' active ingredient to skin areas of crotch, axilla and feet has been found to prevent diaper rash, axillary and foot odor and to alleviate athlete's foot. It has been found that in particular alginic acid and Carbopol resins are particularly useful as the non-toxic, high molecular weight polymeric acid active ingredients for the aforesaid purposes and that the active ingredients can advantageously be used in the form of dusting powders and ointments. The active ingredients can also be dispersed in a suitable pharmaceutical carrier and used to make a stick deodorant and can be dispersed in a suitable liquid carrier to make a spray deodorant and/or aerosol spray deodorant.

The invention may be embodied in other specific forms without departing from the spirit or essential characteristics thereof. The present embodiments are therefore to be considered in all respects as illustrative and not restrictive. The scope of the invention is indicated by the appended claims.

What is claimed is:

1. A method for the treatment and prevention of symptoms of conditions characterized by offensive odor of the body which comprises topically applying to the regions of the body subject to offensive odor a composition comprising:
   (a) from 1 to 30% by weight of a non-toxic, high molecular weight alginic acid, having a molecular weight in the range of from 15,000 to 900,000; and
   (b) from 70 to 99% by weight of a pharmaceutical carrier said alginic acid being applied to said body region in an amount effective to arrest or prevent the development of offensive odor.

2. The method according to claim 1 in which said composition comprises from 2% to 20% by weight of said alginic acid based on the total weight of said composition.

3. The method according to claim 2 in which said composition comprises from 4% to 10% by weight of said alginic acid based on the total weight of the composition.

4. The method according to claim 1 wherein said alginic acid has a molecular weight in the range of from 15,000 to 240,000.

5. The method according to claim 4 in which said composition comprises from 2% to 20% by weight of said alginic acid based on the total weight of the composition.

6. The method according to claim 5 in which said composition comprises from 4% to 10% by weight of said alginic acid based on the total weight of the composition.

7. A method for the treatment and prevention of symptoms of conditions characterized by offensive odor of the body which comprises topically applying to the regions of the body subject to offensive odor a composition comprising:
   (a) from 1 to 30% by weight of a water-soluble non-toxic, high molecular weight organic polymeric acid formed from acrylic acid cross-linked with from 0.75 to 2% of a cross-linking agent selected from the group consisting of polyallyl sucrose and polyallyl pentaerythritol and having a molecular weight of from 450,000 to 5,000,000; and (b) from 70 to 99% by weight of a pharmaceutical carrier said polymeric acid being applied to said body region in an amount effective to arrest or prevent the development of offensive odor.

8. The method according to claim 7 in which said composition comprises from 2% to 20% by weight of said acrylic acid cross-linked polymer based on the total weight of said composition.

9. The method according to claim 8 in which said composition comprises from 4% to 10% by weight of said acrylic acid cross-linked polymer based on the total weight of said composition.

10. A method according to claims 1, 2, 3, 4, 5, 6, 7, 8 or 9 for treating and preventing offensive odor associated with diaper rash which comprises topically applying to an infant in the regions susceptible to producing offensive odor an effective amount of said polymeric acid.

* * * * *